United States Patent
De Weerdt et al.

(10) Patent No.: US 11,519,991 B2
(45) Date of Patent: Dec. 6, 2022

(54) MOTION ESTIMATION AND CORRECTION IN MAGNETIC RESONANCE IMAGING

(71) Applicant: KONINKLIJKE PHILIPS N.V., Eindhoven (NL)

(72) Inventors: Elwin De Weerdt, Tilburg (NL); Nicola Pezzotti, Eindhoven (NL)

(73) Assignee: Koninklijke Philips N.V., Eindhoven (NL)

(*) Notice: Subject to any disclaimer, the term of this patent is extended or adjusted under 35 U.S.C. 154(b) by 0 days.

(21) Appl. No.: 17/320,265

(22) Filed: May 14, 2021

(65) Prior Publication Data
US 2021/0364587 A1   Nov. 25, 2021

(30) Foreign Application Priority Data
May 19, 2020   (EP) .................................... 20175350

(51) Int. Cl.
*G01R 33/561* (2006.01)
*A61B 5/055* (2006.01)
(Continued)

(52) U.S. Cl.
CPC .......... *G01R 33/5611* (2013.01); *A61B 5/055* (2013.01); *G01R 33/482* (2013.01); *G01R 33/5608* (2013.01); *G01R 33/56509* (2013.01)

(58) Field of Classification Search
CPC .......... G01R 33/5608; G01R 33/56509; G01R 33/482; G01R 33/5611; A61B 5/055
See application file for complete search history.

(56) References Cited

U.S. PATENT DOCUMENTS

2012/0243756 A1   9/2012   Samsonov et al.
2013/0088225 A1*  4/2013   Weller ............... G01R 33/5611
                                                         324/322
(Continued)

FOREIGN PATENT DOCUMENTS

| CN | 110942496 A | 3/2020 |
| WO | 2015086415 A1 | 6/2015 |
| WO | 2017009391 A1 | 1/2017 |

OTHER PUBLICATIONS

Oksuz, Ilkay & Clough, James & Ruijsink, Bram & Puyol Anton, Esther & Bustin, Aurélien & Cruz, Gastao & Prieto, Claudia & Rueckert, Daniel & King, Andrew & Schnabel, Julia. (2019). Detection and Correction of Cardiac MR Motion Artefacts during Reconstruction from K-space.

(Continued)

*Primary Examiner* — Gregory H Curran

(57) ABSTRACT

A method of medical imaging including receiving k-space data that is divided into multiple k-space data groups, selecting one of the multiple k-space data groups as a reference k-space data group, and calculating spatial transform data for each of the multiple k-space data groups by inputting the multiple k-space data groups and the reference k-space data group into a transformation estimation module. The spatial transformation estimation module is configured for outputting spatial transform data descriptive of a spatial transform between a reference k-space data group and multiple k-space data groups in response to receiving the reference k-space data group and the multiple k-space data groups as input. The method further comprises reconstructing a corrected magnetic resonance image according to the magnetic resonance imaging protocol using the multiple k-space data groups and the spatial transform data for each of the multiple k-space data groups.

20 Claims, 11 Drawing Sheets

(51) Int. Cl.
    *G01R 33/48*     (2006.01)
    *G01R 33/56*     (2006.01)
    *G01R 33/565*    (2006.01)

(56) References Cited

U.S. PATENT DOCUMENTS

2019/0257905 A1   8/2019   Cheng et al.
2020/0116810 A1   4/2020   Wang et al.

OTHER PUBLICATIONS

Usman, Muhammad & Latif, Siddique & Asim, Muhammad & Qadir, Junaid. (2019). Motion Corrected Multishot MRI Reconstruction Using Generative Networks with Sensitivity Encoding.
Johnson et al "Motion Correction in MRI Using Deep Learning" International Soc. for Magnetic Resonance in Med. ISMRM, No. 4098 Jun. 1, 2018.

\* cited by examiner

MOTION ESTIMATION AND CORRECTION IN MAGNETIC RESONANCE IMAGING

CROSS-REFERENCE TO PRIOR APPLICATIONS

This application claims the benefit of EP Application No. 20175350.6, filed on May 19, 2020, which is incorporated by reference herein.

TECHNICAL FIELD

The invention relates to Magnetic Resonance Imaging, in particular to the correction of motion artifacts in magnetic resonance images.

BACKGROUND OF THE INVENTION

A large static magnetic field is used by Magnetic Resonance Imaging (MRI) scanners to align the nuclear spins of atoms as part of the procedure for producing images within the body of a patient. This large static magnetic field is referred to as the BO field or the main magnetic field. Various quantities or properties of the subject can be measured spatially using MRI. A difficulty in magnetic resonance imaging is that the k-space data, from which the images are reconstructed, may be acquired of an extended period of time. Voluntary and involuntary motion of the subject being imaged can lead to image artifacts and degradation.

United States patent application publication US20120243756A1 discloses method for reconstructing a motion-compensated image depicting a subject with a magnetic resonance imaging (MRI) system. An MRI system is used to acquire a time series of k-space data from the subject by sampling k-space along non-Cartesian trajectories, such as radial, spiral, or other trajectories at a plurality of time frames. Those time frames at which motion occurred are identified and this information used to segment the time series into a plurality of k-space data subsets. For example, the k-space data subsets contain k-space data acquired at temporally adjacent time frames that occur between those identified time frames at which motion occurred. Motion correction parameters are determined from the k-space data subsets. Using the determined motion correction parameters, the k-space data subsets are corrected for motion. The corrected data subsets are combined to form a corrected k-space data set, from which a motion-compensated image is reconstructed. That is, correction of motion is done for a Propeller (radial) sampling strategy with blades that overlap in the center region of k-space to generate redundancy in the k-space data from which motion can be corrected for. The US patent application US2020/0116810 concerns motion correction on the basis of a spiral scanning to sample k-space data. This known motion correction makes use of a variable density sampling pattern to sample the inner portion of k-space at a sampling density higher than the Nyquist criterion.

SUMMARY OF THE INVENTION

The invention provides for a medical system, a computer program, and a method in the independent claims. Embodiments are given in the dependent claims.

Embodiments may provide for an improved method of motion correction in magnetic resonance imaging. The k-space for an image reconstruction has been divided into multiple k-space groups. One of these is selected as a reference k-space data group. The k-space data group is then compared to each of the multiple k-space groups to calculate spatial transform data using a spatial transformation estimation module. The multiple k-space data groups and the spatial transform data may then be used to reconstruct a corrected magnetic resonance image. An advantage of this approach may be that it also provides for motion correction even with a cartesian sampling pattern in k-space.

The spatial transformation estimation module can be implemented in several different ways. In one example, the spatial transformation estimation module can be implemented so that the groups of k-space data are input in image space. The multiple k-space data groups are first converted into intermediate magnetic resonance images using an intermediate magnetic resonance image reconstruction neural network. Since the groups of k-space data are each only a portion of the full k-space acquisition they are under sampled. However, the use of a neural network enables the construction of intermediate magnetic resonance images that contain the large spatial features. This for example enables the use of a standard rigid motion registration algorithm to be used to calculate the spatial transform. Standard reconstruction algorithms can then be used to correct for motion artifacts.

Another approach is to implement the spatial transformation estimation module as a neural network that takes the k-space data as an input. In this case the neural network replaces both the intermediate magnetic resonance image reconstruction neural network and the standard rigid motion registration algorithm.

The medical system is configured to arrange for reconstruction of the set of magnetic resonance images in that reconstruction software is installed in the computational system or in that the computational system has access to a remote reconstruction facility. The reconstruction software may be installed on a remote server, e.g. in the healthcare institution of even accessible to a data-network in that the reconstruction software may be available in 'the cloud', In these remote configurations the computational system is equipped with functionality to arrange for reconstruction of the set of magnetic resonance images at the remotely located reconstruction function. The trained neural network may be incorporated in te magnetic resonance imaging system's computational system. Alternatively, the computational system may be provided with access to the trained neural network that is located remote from the (physical hardware of the) magnetic resonance imaging system, e.g. on a local server of the healthcare institution or the trained neural network may be accessible in 'the cloud'.

In one aspect the invention provides for a medical system that comprises a memory storing machine-executable instructions and a spatial transformation estimation module. The spatial transformation estimation module is configured for outputting spatial transform data descriptive of a spatial transformation between a reference k-space data group and multiple k-space data groups in response to receiving the reference k-space data group and the multiple k-space data groups as input. The reference k-space data group is magnetic resonance imaging k-space data. The multiple k-space data groups are also magnetic resonance imaging k-space data. This means that the reference k-space data group may be reconstructed into a magnetic resonance image. The multiple k-space data groups may also be reconstructed into magnetic resonance images. The spatial transform may then be a spatial transform in image space between these images if they were reconstructed.

The spatial transformation estimation module in some embodiments may for example be a neural network. In this case the neural network can be trained to receive the reference k-space data group and each of the multiple k-space data groups to construct the spatial transform without doing the intermediate image reconstruction. In other examples the spatial transformation estimation module may receive the reference k-space data group in the form of an intermediate magnetic resonance image. The spatial transformation estimation module may also be configured to receive each of the multiple k-space data groups also in the form of an intermediate magnetic resonance image.

The medical system further comprises a computational system. The computational system may take different forms in different examples. In one example the computational system is a workstation or computer system controlling a magnetic resonance imaging system. In another example the computational system could be a PC or workstation used by a radiology department for the reconstruction and examination of magnetic resonance images. In yet another example the medical system could be a server or virtual machine accessing via the internet or web that performs image reconstructions.

Execution of the machine-executable instructions causes the computational system to receive k-space data acquired according to a magnetic resonance imaging protocol. The k-space data is divided into multiple k-space data groups. The k-space data may represent the full amount of k-space data for performing the image reconstruction. However, this k-space data can be broken into smaller groups which are known as the multiple k-space data groups. These for example could be grouped in different ways according to the shots that are acquired or based on the acquisition time. For this reason, the multiple k-space data groups may represent different motion states or positions of the subject that was imaged.

Execution of the machine-executable instructions further causes the computational system to select one of the multiple k-space data groups as the reference k-space data group. In this case there may be more or less a free choice of which one is selected as the reference k-space data group. This is then used as a comparison to the others of the multiple k-space data groups to determine the spatial transform. In some instances, there may be a monitor or system which monitors the motion of the subject and the k-space data which represents the least motion or original position of the subject could be selected. This is however not necessary.

Execution of the machine-executable instructions further causes the computational system to calculate the spatial transform data for each of the multiple k-space data groups by inputting the multiple k-space data groups and the reference k-space data group into the spatial transformation estimation module. Execution of the machine-executable instructions further causes the computational system to reconstruct the corrected magnetic resonance image according to the magnetic resonance imaging protocol using the multiple k-space data groups and the spatial transform data for each of the multiple k-space data groups. The reconstruction of the corrected magnetic resonance image is therefore very flexible. Standard reconstruction techniques which use information about the motion of the subject may be used. In the case of a rigid transformation the k-space data may be readily transformed. In other instances, the spatial transform may be used to set up an optimization problem to reconstruct the corrected magnetic resonance image. Once the spatial transform is known, well known and trusted algorithms can be used to reconstruct the corrected magnetic resonance image.

The present invention concerns a medical system for reconstruction of a magnetic resonance image from k-space data sets sampled along a Cartesian sampling pattern in k-space from disjoint k-space data groups. That is, there are no k-space points for which k-space data are sampled in more than one k-space data group. Accordingly, there is no redundancy among the multiple k-space data groups. Further, the intermediate magnetic resonance imaging reconstruction neural network is configured to output an intermediate magnetic resonance image in response to receiving a respective k-space data group. That is, for each k-space data group an intermediate magnetic resonance image is reconstructed. In practice these intermediate magnetic resonance images do not or hardly have diagnostic quality because they derive from a single k-space data group that only covers a (very) partial region of k-space. An insight of the present invention is that nevertheless the intermediate magnetic resonance images represent sufficient information to discern (course) image structures from which spatial transformations can be derived between each of the k-space data groups and the selected reference k-space data group. Because the collection of k-space data groups together cover k-space for the ultimate spatial reconstruction at which the corrected magnetic resonance image is reconstructed, the spatial transformations also represent motion details at this ultimate spatial reconstruction that corresponds to the true acquisition voxel size. Motion correction of the present invention corrects for motion that occurs between the acquisitions of the respective disjoint k-space data groups.

The invention achieves correction for motion that occurs between the acquisitions of respective Cartesian sampled k-space data sets. The present invention expands the concept of k-space data driven motion correction that is generally known from radial (multi-vane or propeller techniques), spiral and other non-Cartesian sampling strategies to application with Cartesian sampling strategies that have far less redundancy in the k-space data.

In another embodiment the multiple k-space data groups are disjoint. By disjoint it means that the k-space data does not resample the same points. In another example being disjoint may mean that there is a minimum space or distance within k-space between each of the multiple k-space data groups. This may have a benefit over some techniques where the central region of k-space is repeatedly sampled over and over again for a self-navigation technique.

In another embodiment the multiple k-space data groups are distributed in k-space.

In another embodiment each of the multiple k-space data groups are distributed uniformly in k-space. This means that for example the central region of the k-space data is not oversampled.

In another embodiment each of the multiple k-space data groups is undersampled. For example, the gross motion of a subject can be noted by looking at the larger structures within the image. This sort of structure is also evident in images that are reconstructed from undersampled k-space data. This may therefore enable the self-navigation or correction of motion for magnetic resonance imaging the acquisition of less k-space data.

In another embodiment reconstruction of the corrected magnetic resonance image is at least partially performed by calculating corrected multiple k-space data groups using the multiple k-space data groups and the spatial transform data for each of the multiple k-space data groups. If it is known how the subject has moved for each of the multiple k-space data groups relative to the reference k-space data group then it is possible to calculate corrected or resampled k-space data. In the case of a rigid body transformation this is very straightforward because it represents a transformation in the k-space data. This may include a repositioning of the k-space data as well as a phase correction. Once the corrected multiple k-space data groups are calculated a standard magnetic resonance imaging algorithm can then be used to reconstruct the corrected magnetic resonance image.

In another embodiment the reconstruction of the corrected magnetic resonance image is performed as an optimization problem. Another example is to incorporate the spatial transform information in the forward model of the optimization problem. A specific example is the case of rigid motion that can be represented by an additional matrix multiplication.

In another embodiment the memory further contains a final magnetic resonance image reconstruction neural network configured to output a corrected magnetic resonance image in response to receiving multiple k-space data groups and the spatial transform data for each of the multiple k-space data groups. The reconstruction of the corrected magnetic resonance image is performed by inputting the multiple k-space data groups and the spatial transform data for each of the multiple k-space data groups into the final magnetic resonance image reconstruction neural network. For example, the neural network could be trained by using sets of training data which comprise a motion corrected magnetic resonance image and the k-space data groups that were used to reconstruct this image.

In another embodiment execution of the machine-executable instructions further causes the computational system to divide the k-space data into multiple k-space data groups according to any one of the following: by acquisition shots, by an acquisition time, by an acquisition channel, a motion signal descriptive of subject motion, and combinations thereof. In techniques such as parallel imaging where more than one receive channel or antenna is used the magnetic resonance imaging data may be grouped by the acquisition channel. This may for example be useful in enforcing data consistency between the various acquisition channels.

In another embodiment the memory further contains an intermediate magnetic resonance imaging reconstruction neural network. The intermediate magnetic resonance imaging reconstruction neural network is configured to output an intermediate magnetic resonance image in response to receiving a k-space data group. The spatial transformation estimation module is configured to receive the multiple k-space data groups as the intermediate magnetic resonance image for each of the multiple k-space data groups. In other words, instead of inputting the multiple k-space data groups directly into the spatial transformation estimation module, instead the multiple k-space data groups are first transformed into an intermediate magnetic resonance image and then input into the spatial transformation estimation module. Likewise, the spatial transformation estimation module is configured to receive the reference k-space data group as the intermediate magnetic resonance image for the reference k-space data group. This may for example increase the flexibility of the medical system.

The intermediate magnetic resonance imaging reconstruction neural network for example may be useful in constructing intermediate magnetic resonance images which are useful for registering to each other to determine the spatial transform. In this case standard registration algorithms can be used. The use of the intermediate magnetic resonance imaging reconstruction neural network may also enable better motion correction. For example, if it is known what type of image is being made then this is additional information which the intermediate magnetic resonance imaging reconstruction neural network can use to further reduce the amount of sampling which is useful for producing an image which can be used for detecting motion.

Execution of the machine-executable instructions further causes the computational system to receive the intermediate magnetic resonance image for each of the multiple k-space data groups by inputting each of the multiple k-space data groups into the intermediate magnetic resonance imaging reconstruction neural network.

In another embodiment the spatial transformation estimation module is implemented using a rigid body registration or a spatial transformation estimating neural network. In the rigid body registration standard algorithms may be used to determine a rigid motion or transformation between different images. The spatial transformation estimation neural network can be a neural network which has been trained using training data which has a translation or transformation between the two images. Once the training data is available the spatial transformation estimation neural network may be trained using for example a deep learning algorithm.

In another embodiment the k-space sampling pattern is Cartesian. The magnetic resonance imaging protocol is a parallel imaging magnetic resonance imaging protocol. This embodiment may be beneficial because typically it is difficult to do motion correction with a Cartesian sampling pattern. Normally the central region of k-space is heavily oversampled. Particularly, when a neural network is used to reconstruct intermediate magnetic resonance images from the groups of k-space data, this enables the use of a Cartesian sampling pattern.

In another embodiment the medical system further comprises a magnetic resonance imaging system. The memory further contains pulse sequence commands configured for acquiring the k-space data according to the magnetic resonance imaging protocol. Execution of the machine-executable instructions further causes the computational system to acquire the k-space data by controlling the magnetic resonance imaging system with the pulse sequence commands.

In another embodiment the magnetic resonance imaging system comprises a radio-frequency system with multiple receive channels. The magnetic resonance imaging protocol is a parallel imaging magnetic resonance imaging protocol. Execution of the machine-executable instructions further causes the computational system to divide the k-space data into the multiple k-space data groups at least partially according to the receive channels. Dividing these by the receive channels may have the benefit that the determination of the spatial transform enforces data consistency between the data acquired on different channels.

In another embodiment, the machine-executable instructions further causes the computational system to divide the k-space data into multiple k-space data groups at least partially according to any one of the following: by the acquisition shot or shots, by an acquisition time or acquisition interval, and combinations thereof. The shot is a reference to a group of k-space data that was acquired as a row or line in k-space as a single acquisition. It makes sense to group the data according to this. Another way of grouping the data is that the subject may move over time. By dividing the acquisition time or intervals into groups based on the acquisition time it may provide for a good means of correcting for periodic motion or other motion of the subject without monitoring the subject motion.

In another embodiment the medical system further comprises a subject motion monitor that is configured for generating subject motion data that is descriptive of a motion or position of the subject. This for example could be a camera or other device which obtains an image of the subject and derives the subject motion data. Other devices include a respiration belt, an object for measuring the respiration of the subject, or even an ECG system which may be used for monitoring a heart phase of the subject. Execution of the machine-executable instructions further causes the computational system to control the subject motion monitor to acquire the subject motion data during the acquisition of the k-space data. The subject motion data may then be referenced or indexed to the k-space data so that the k-space data is described or labeled in terms of the subject motion data. Execution of the machine-executable instructions further causes the computational system to divide the k-space data into the multiple k-space data groups at least partially according to the subject motion data. In this case, the k-space data can be sorted according to the position or motion state of the subject. This may also provide for improved motion correction.

In another embodiment the invention provides for a method of medical imaging. The method comprises receiving the k-space data acquired according to a magnetic resonance imaging protocol. The k-space data is divided into multiple k-space data groups. The method further comprises selecting one of the multiple k-space data groups as a reference k-space data group.

The method further comprises calculating spatial transform data for each of the multiple k-space data groups by inputting the multiple k-space data groups and the reference k-space data group into a spatial transformation estimation module. The spatial transformation estimation module is configured for outputting spatial transform data descriptive of a spatial transform between a reference k-space data group and the multiple k-space data groups in response to receiving the reference k-space data group and the multiple k-space data groups as input.

The method further comprises reconstructing the corrected magnetic resonance image according to the magnetic resonance imaging protocol using the multiple k-space data groups and the spatial transform data for each of the multiple k-space data groups.

In another aspect the invention provides for a computer program comprising machine-executable instructions for execution by a computational system. The computer program may for example be stored on a non-transitory storage medium. Execution of the machine-executable instructions causes the computational system to receive k-space data acquired according to a magnetic resonance imaging protocol. The k-space data is divided into multiple k-space data groups. Execution of the machine-executable instructions further causes the computational system to select one of the multiple k-space data groups as a reference k-space data group.

Execution of the machine-executable instructions further causes the computational system to calculate spatial transform data for each of the multiple k-space data groups by inputting the multiple k-space data groups and the reference k-space data group into a spatial transformation estimation module. The spatial transformation estimation module is configured for outputting spatial transform data descriptive of a spatial transform between a reference k-space data group and each of multiple k-space data groups in response to receiving the reference k-space data group and the multiple k-space data groups as input. Execution of the machine-executable instructions further causes the computational system to reconstruct the corrected magnetic resonance image according to the magnetic resonance imaging protocol using the multiple k-space data groups and the spatial transform data for each of the multiple k-space data groups.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor or computational system of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the computational system of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the computational system. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a computational system. 'Computer storage' or 'storage' is a further example of a computer-readable storage medium. Computer storage is any non-volatile computer-readable storage medium. In some embodiments computer storage may also be computer memory or vice versa.

A 'computational system' as used herein encompasses an electronic component which is able to execute a program or machine executable instruction or computer executable code. References to the computational system comprising the example of "a computational system" should be interpreted as possibly containing more than one computational system or processing core. The computational system may for instance be a multi-core processor. A computational system may also refer to a collection of computational systems within a single computer system or distributed amongst multiple computer systems. The term computational system should also be interpreted to possibly refer to a collection or network of computing devices each comprising a processor or computational systems. The machine executable code or instructions may be executed by multiple computational systems or processors that may be within the same computing device or which may even be distributed across multiple computing devices.

Machine executable instructions or computer executable code may comprise instructions or a program which causes a processor or other computational system to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances, the computer executable code may be in the form of a high-level language or in a pre-compiled form and be used in conjunction with an interpreter which generates the machine executable instructions on the fly. In other instances, the machine executable instructions or computer executable code may be in the form of programming for programmable logic gate arrays.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a computational system of a general purpose computer, special purpose computer, or other programmable data processing apparatus to produce a machine, such that the instructions, which execute via the computational system of the computer or other programmable data processing apparatus, create means for implementing the functions/acts specified in the flowchart and/or block diagram block or blocks.

These machine executable instructions or computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The machine executable instructions or computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer to indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the computational system of a computer system to interact with and/or control an external computing device and/or apparatus. A hardware interface may allow a computational system to send control signals or instructions to an external computing device and/or apparatus. A hardware interface may also enable a computational system to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

K-space data is defined herein as being the recorded measurements of radio frequency signals emitted by atomic spins using the antenna of a Magnetic resonance apparatus during a magnetic resonance imaging scan. Magnetic resonance data is an example of tomographic medical image data.

A Magnetic Resonance Imaging (MRI) image, MR image, or magnetic resonance imaging data is defined herein as being the reconstructed two- or three-dimensional visualization of anatomic data contained within the k-space data. This visualization can be performed using a computer.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
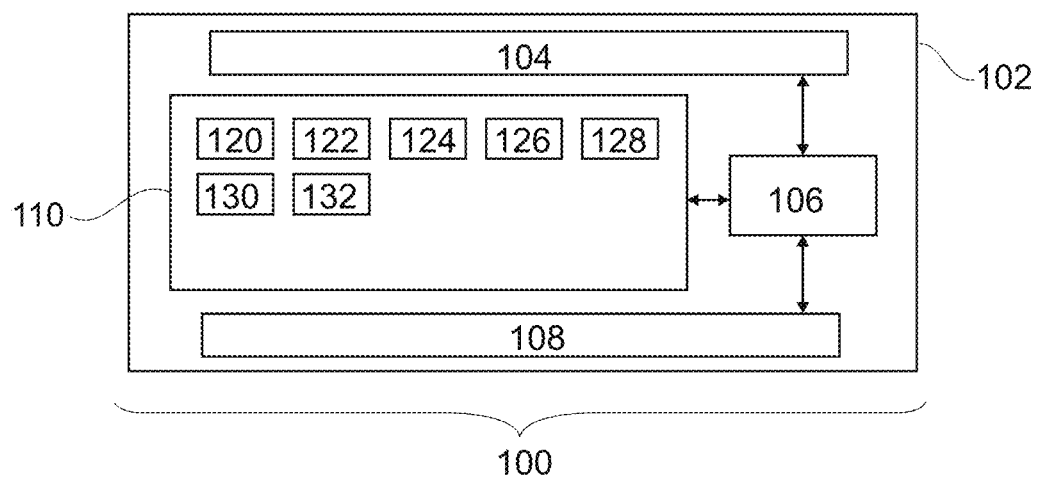
FIG. 1 illustrates an example of a medical system.

FIG. 1 illustrates an example of a medical system 100. In FIG. 1 the medical system 100 is a computer 102. The computer 102 is shown as comprising a computational system 106. The computer 102 is intended to represent one or more computer systems that may possibly be networked and working cooperatively. The computational system 106 may for example be one or more processors located at one or more locations. The computer 102 is further shown as containing an optional hardware interface 104. If other components are present the computational system 106 may use the hardware interface 104 to communicate and control these additional components. The computational system 106 is also additionally shown as being connected to an optional user interface 108. The user interface 108 may for example be used by an operator to control the operation and function of the medical system 100. A memory 110 is further shown as being connected to the computational system 106. The memory 110 is intended to represent any combination of memories or memory devices which may be accessible to the computational system 106. In some examples the memory 110 may be a non-transitory storage medium.

The memory 110 is shown as containing machine-executable instructions 120. The machine-executable instructions 120 enable the computational system 106 to control the operation and function of the medical system 100. The machine-executable instructions 120 may also enable the computational system 106 to perform data processing and image processing tasks. The memory 110 is further shown as containing a spatial transformation estimation module 122. The memory 110 is further shown as containing k-space data 124. The k-space data 124 is acquired according to a magnetic resonance imaging protocol. The memory 110 is further shown as containing multiple k-space data groups 126. The k-space data 124 has been divided into the multiple k-space data groups 126.

The memory 110 is further shown as containing a reference k-space data group 128. The reference k-space data group 128 is selected from the multiple k-space data groups 126. The memory 110 is further shown as containing spatial transform data 130 for each member of the multiple k-space data groups 126. The spatial transform data 130 is descriptive of a spatial transform between the reference k-space data group 128 and the multiple k-space data groups 126 in image space. The reference k-space data group 128 and the multiple k-space data groups 126 may be input into the spatial transformation estimation module 122 in either k-space or in image space. For example, the reference k-space data group 128 and the multiple k-space data groups 126 could be transformed into image space before being input into the spatial transformation estimation module 122. The memory 110 is further shown as containing a corrected magnetic resonance image 132 that has been reconstructed using the spatial transform data 130 for each of the multiple k-space data groups 126. This may be performed in a variety of different ways. In one example the spatial transform data 130 is used to correct or resample the multiple k-space data groups 126 before a conventional reconstruction algorithm is applied. In another example a neural network may take as input the spatial transform data 130 and the multiple k-space data groups 126 and then output a corrected magnetic resonance image 132. In yet another example, a conventional magnetic resonance imaging reconstruction algorithm may be posed as an optimization problem. In this example the spatial transform data 130 is used in the optimization problem to reconstruct the multiple k-space data groups 126 into the corrected magnetic resonance image 132.

Figure 2:
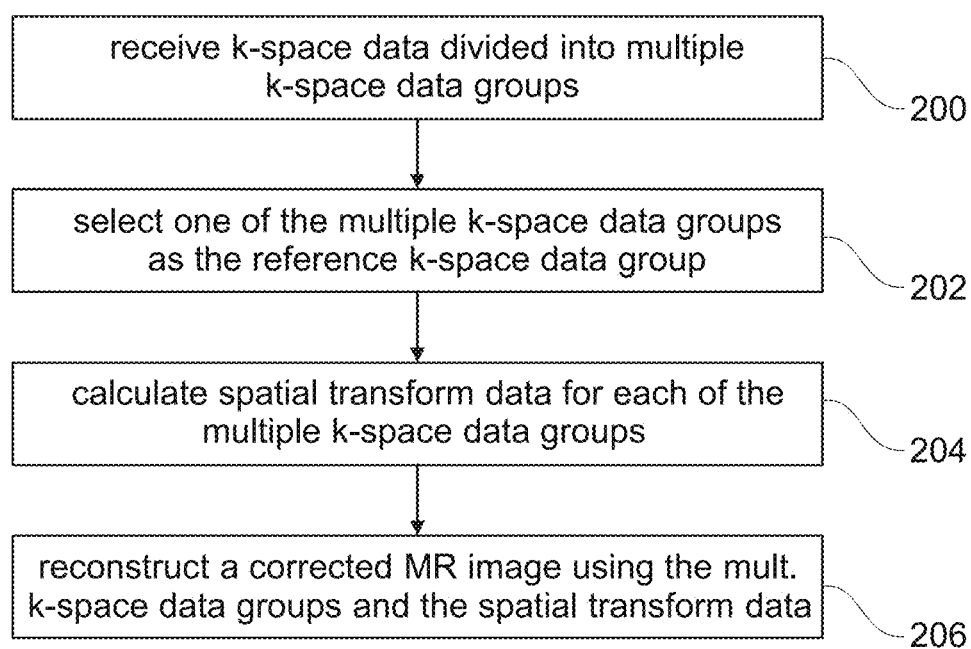
FIG. 2 shows a flow chart which illustrates a method of operating the medical system of FIG. 1.

FIG. 2 shows a flowchart which illustrates a method of operating the medical system 100 of FIG. 1. First in step 200 the k-space data 124 is received. The k-space data 124 has been divided into the multiple k-space data groups 126. Next in step 202, one of the multiple k-space data groups 126 is selected as the reference k-space data group 128. Then in step 204, the spatial transform data 130 is calculated by inputting the reference k-space data group 128 and the multiple k-space data groups 126 into the spatial transformation estimation module 122. Finally, in step 206, the corrected magnetic resonance image 132 is calculated using the spatial transform data 130 and the multiple k-space data groups 126.

Figure 3:
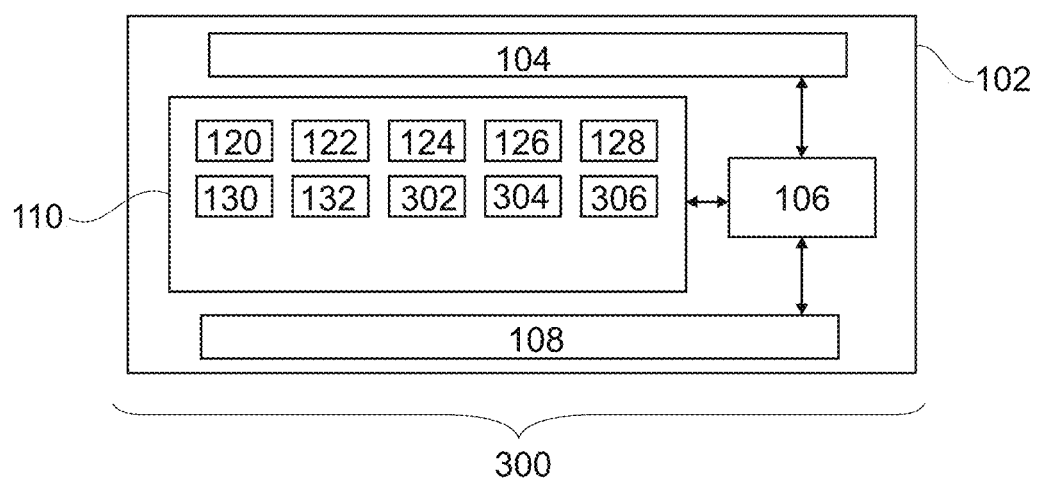
FIG. 3 illustrates a further example of a medical system.

FIG. 3 illustrates a further example of a medical system 300. The medical system 300 in FIG. 3 is similar to the medical system 100 depicted in FIG. 1. The medical system 300 in FIG. 3 is shown as additionally comprising an intermediate magnetic resonance imaging reconstruction neural network 302. Each of the multiple k-space data groups 126 can be input into the intermediate magnetic resonance imaging reconstruction neural network 302 and in response, the intermediate magnetic resonance images 304 are output. This may be advantageous because the intermediate magnetic resonance imaging reconstruction neural network 302 can be used to reconstruct an intermediate magnetic resonance image 304 using less k-space data than in a conventional reconstruction algorithm. The intermediate magnetic resonance images 304 are not intended to be of diagnostic quality. However, the large structures and rough outline of features in the image are visible with less degree of sampling and in particular, when a neural network is used to reconstruct them.

For example, the neural network 302 can be configured for reconstructing a particular type of magnetic resonance image or even data about the type of scan may be input into it. This is additional information which can be used to aid in reconstructing the image. The intermediate magnetic resonance images 304 may for example not be of sufficient quality for diagnostic use but they are sufficient for determining the spatial transform data 130. The memory 110 is also shown as containing a reference magnetic resonance image 306 which is one of the intermediate magnetic resonance images 304 and plays the same part as the reference k-space data group 128. In image space well known registration algorithms can be used to make a registration between the reference magnetic resonance image 306 and the intermediate magnetic resonance images 304. This enables the spatial transform data 130 to be calculated readily.

Figure 4:
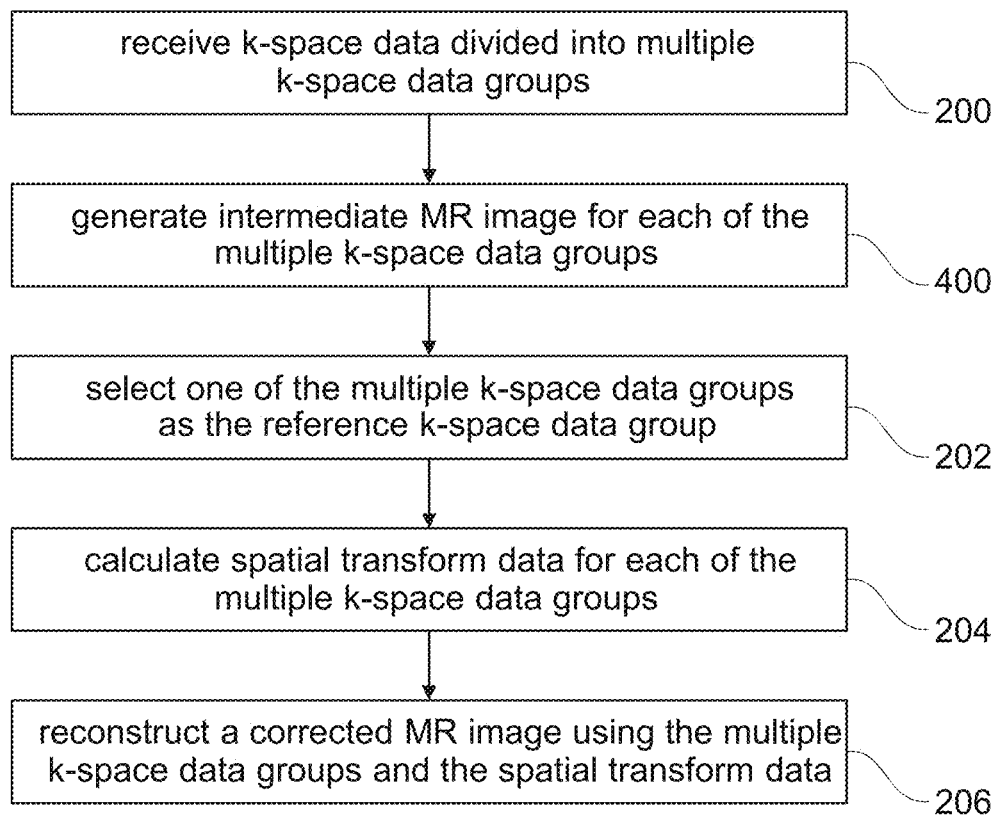
FIG. 4 shows a flow chart which illustrates a method of operating the medical system of FIG. 3.

FIG. 4 illustrates a flowchart which shows a method of operating the medical system 300 of FIG. 3. The method depicted in FIG. 4 is similar to the method depicted in FIG. 2. The method in FIG. 4 starts with step 200 of FIG. 2. Next, in step 400, the multiple k-space data groups 126 are input into the intermediate magnetic resonance imaging reconstruction neural network 302 and the intermediate magnetic resonance images 304 are output. Step 202 is the same as in FIG. 1. Step 204 is also equivalent to step 204 in FIG. 2. However, in this case, the k-space data is essentially input into the spatial transformation estimation module 122 in image space. Steps 206 in FIGS. 4 and 2 are also equivalent.

Figure 5:
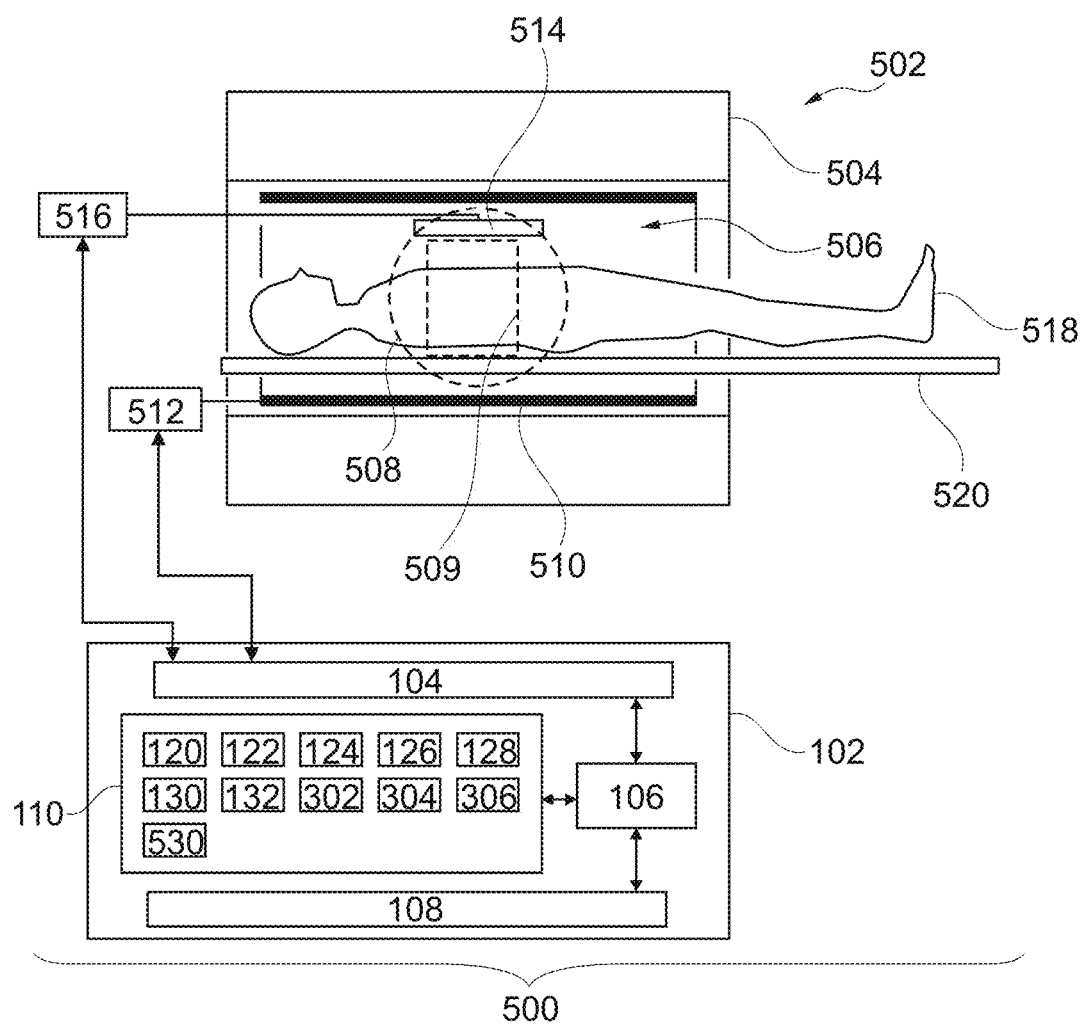
FIG. 5 illustrates an example of a medical system.

FIG. 5 illustrates a further example of a medical system 500. The medical system 500 is similar to the medical system 300 in FIG. 3 except the medical system 500 in FIG. 5 further comprises a magnetic resonance imaging system 502.

The magnetic resonance imaging system 502 comprises a magnet 504. The magnet 504 is a superconducting cylindrical type magnet with a bore 506 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils.

Within the bore 506 of the cylindrical magnet 504 there is an imaging zone 508 where the magnetic field is strong and uniform enough to perform magnetic resonance imaging. A region of interest 509 is shown within the imaging zone 508. The magnetic resonance data that is acquired typically acquired for the region of interest. A subject 518 is shown as being supported by a subject support 520 such that at least a portion of the subject 518 is within the imaging zone 508 and the region of interest 509.

Within the bore 506 of the magnet there is also a set of magnetic field gradient coils 510 which is used for acquisition of preliminary magnetic resonance data to spatially encode magnetic spins within the imaging zone 508 of the magnet 504. The magnetic field gradient coils 510 connected to a magnetic field gradient coil power supply 512. The magnetic field gradient coils 510 are intended to be representative. Typically magnetic field gradient coils 510 contain three separate sets of coils for spatially encoding in three orthogonal spatial directions. A magnetic field gradient power supply supplies current to the magnetic field gradient coils. The current supplied to the magnetic field gradient coils 510 is controlled as a function of time and may be ramped or pulsed.

Adjacent to the imaging zone 508 is a radio-frequency coil 514 for manipulating the orientations of magnetic spins within the imaging zone 508 and for receiving radio transmissions from spins also within the imaging zone 508. The radio frequency antenna may contain multiple coil elements. The radio frequency antenna may also be referred to as a channel or antenna. The radio-frequency coil 514 is connected to a radio frequency transceiver 516. The radio-frequency coil 514 and radio frequency transceiver 516 may be replaced by separate transmit and receive coils and a separate transmitter and receiver. It is understood that the radio-frequency coil 514 and the radio frequency transceiver 516 are representative. The radio-frequency coil 514 is intended to also represent a dedicated transmit antenna and a dedicated receive antenna. Likewise the transceiver 516 may also represent a separate transmitter and receivers. The radio-frequency coil 514 may also have multiple receive/transmit elements and the radio frequency transceiver 516 may have multiple receive/transmit channels. For example if a parallel imaging technique such as SENSE is performed, the radio-frequency could 514 will have multiple coil elements.

The transceiver 516 and the gradient controller 512 are shown as being connected to the hardware interface 106 of a computer system 102.

The memory 110 is further shown as containing pulse sequence commands 530. The pulse sequence commands are commands or data which may be converted into commands for controlling the magnetic resonance imaging system 502 to acquire the k-space data 124.

Figure 6:
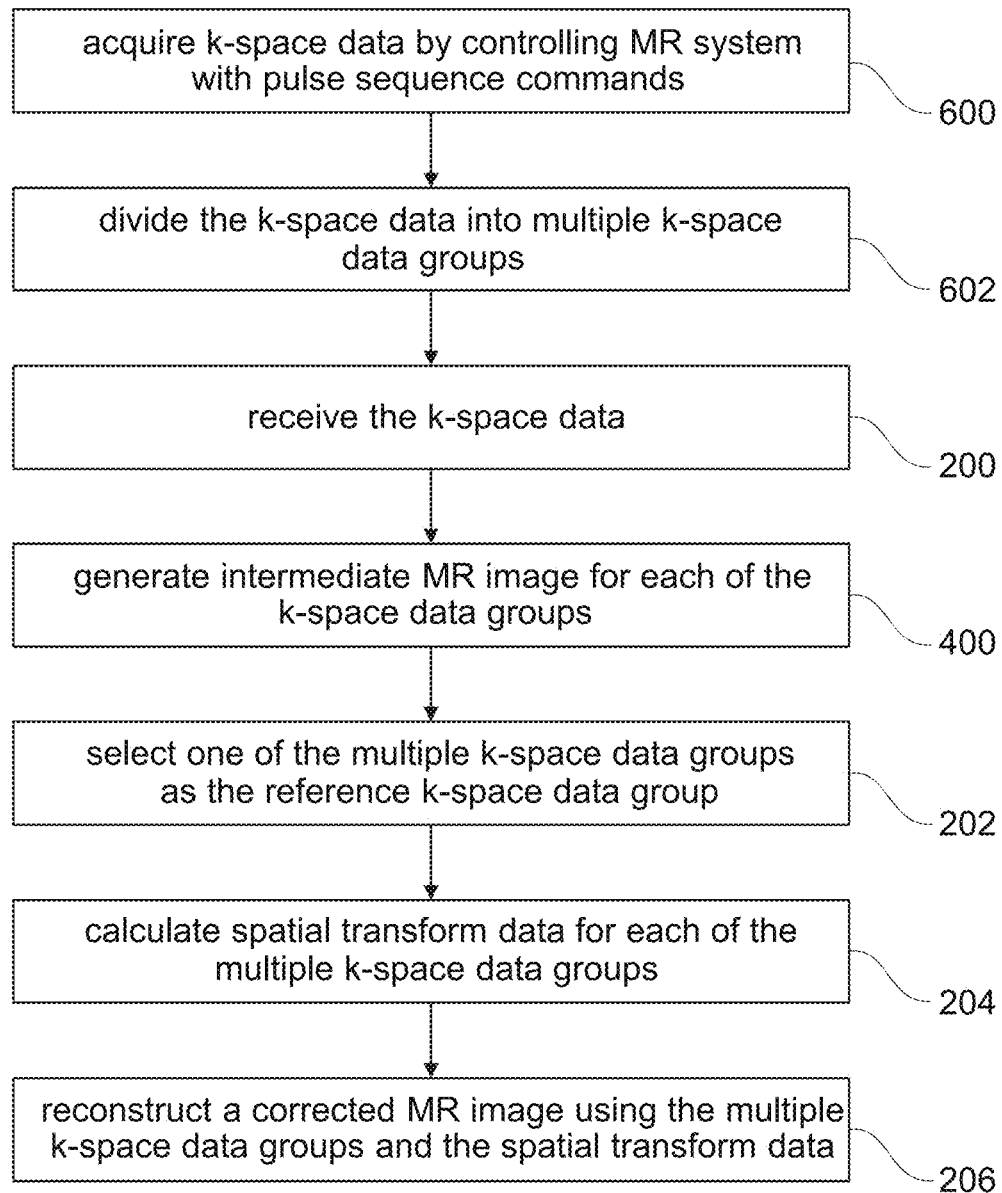
FIG. 6 shows a flow chart which illustrates a method of operating the medical system of FIG. 5.

FIG. 6 shows a flowchart which illustrates a method of operating the medical system 500 of FIG. 5. The method illustrated in FIG. 6 is similar to the method illustrated in FIG. 4 except several additional steps are performed. In step 600 the magnetic resonance imaging 500 is controlled with the pulse sequence commands 530 to acquire the k-space data 124. Next, in step 602, the k-space data 124 is divided into the multiple k-space data groups 126. This can be performed in a variety of ways. For example, the pulse sequence commands 530 may be configured to acquire lines of k-space data. These are so called shots of k-space data. This is the data that is acquired during a single acquisition. Grouping the k-space data 124 into the shots or the acquisition may be a natural division. Another way would be to divide the k-space data according to time intervals. After step 602 is performed the method proceeds to step 200 as is illustrated in FIG. 4

Figure 7:
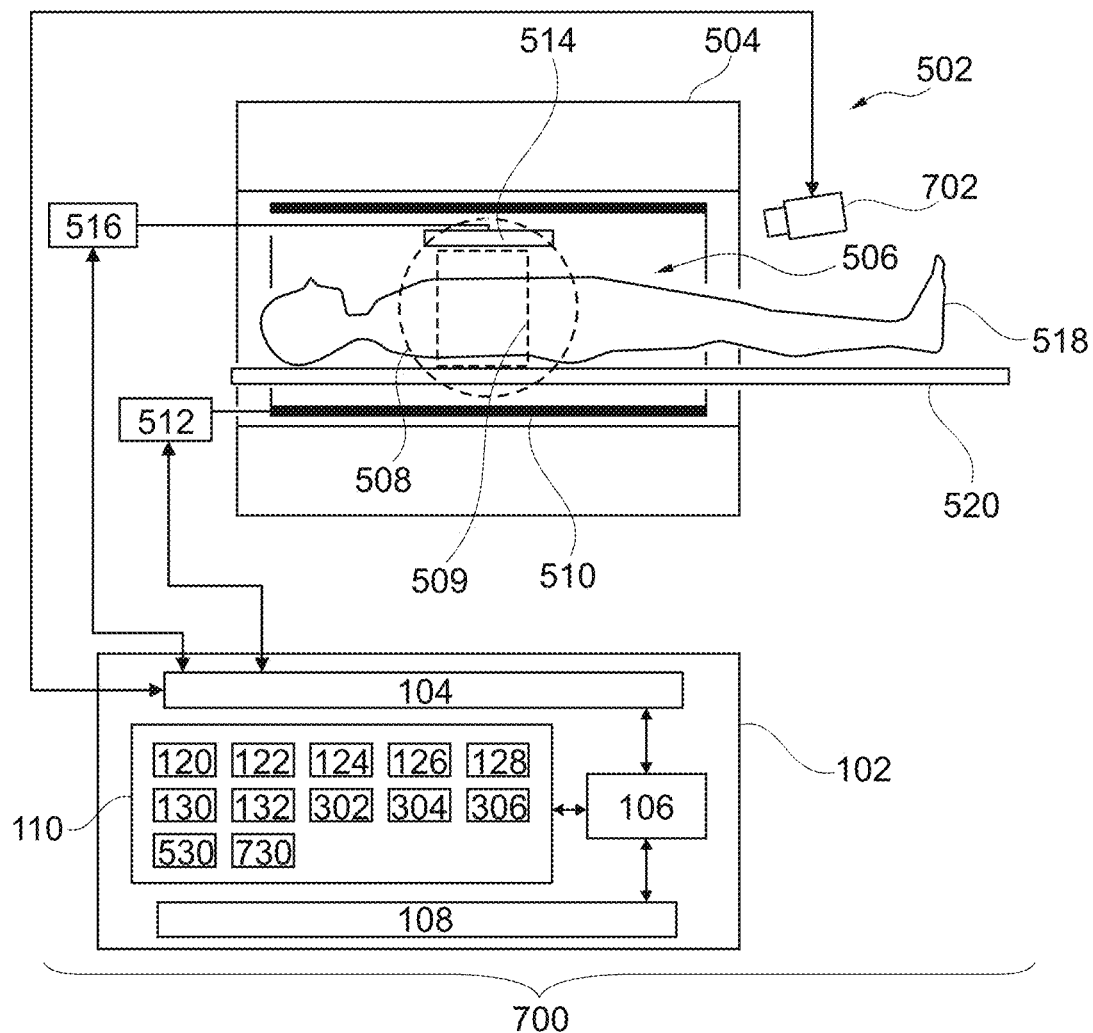
FIG. 7 illustrates a further example of a medical system.

FIG. 7 illustrates a further example of the medical system 700. The medical system 700 is similar to the medical system 500 in FIG. 5 except it additionally comprises a subject motion monitor 702. In this example the subject motion monitor 702 is depicted as a camera which can take images of the subject 518 during the acquisition of the k-space data 124. The camera 702 however, is intended to be representative and there may for example be other devices which are used to monitor the motion of the subject 518. For example, the subject motion monitor may also be a respiratory belt or other device such as an ECG to monitor repetitive motion of the subject 518. The machine-executable instructions 120 are configured such that during the acquisition of the k-space data 124 subject motion data 730 is also acquired by the subject motion monitor 702. The subject motion data 730 may then provide a numerical value or measure of the motion of the subject 518 such that the k-space data 124 can be divided into the multiple k-space data groups 126 using the subject motion data 730.

Some examples may use Neural Network or Deep Learning based solutions can reconstruct reasonable, but non-diagnostic, images from highly accelerated scans. A point is that the majority of structures (e.g. bone, skin, large organ) are reliably reconstructed (while small structures get lost) and that the main edges of these larger structures are sufficient to estimate (rigid and non-rigid) motion parameters.

Once motion parameters are estimated, a standard magnetic resonance imaging reconstruction algorithm (or AI based recon) may utilize this information to reconstruct images without motion corruption (reconstruct the corrected magnetic resonance image 132). This approach is valid for the majority of acquisition strategy (non-Cartesian and Cartesian).

Patient motion during scans always degrades image quality (IQ) and in many cases a rescan is required or the diagnostic quality is reduced making it harder to make a diagnosis. Examples may provide a means for detecting, estimating and subsequently removing/reducing the effects of motion on the data.

Examples may incorporate Artificial Intelligence (AI) based solutions can reconstruct reasonable, but non-diagnostic, images from highly accelerated scans where the majority of the structures (e.g. bone, skin, large organ) are reliably reconstructed (while small structures get lost) (more details are given in ppt at end of the document).

Examples may also use the main edges of larger structures are sufficient (in the intermediate magnetic resonance images 304) to estimate (rigid and non-rigid) motion parameters.

The ability of neural network or AI to reconstruct the main parts (contours/edges) from major structure comes from the fact that these structures dominate the signal in k-space (e.g. have high SNR). Smaller details generate lower SNR signal and hence when undersampling these are get 'lost' first. Without the smaller details many (if not all) images are non-diagnostic.

This means that this can be used in normal scanning scenarios for which enough data is acquired to created diagnostic images. It is expected that the amount of data required for getting the contours/edges of the majority of main structures right is 3 to 5 times less than that of the whole scan.

This in turn implies that examples can be used to detect, estimate, and correct for incidental motion with up to 3 to 5 different motion states in one scan.

Examples can possibly be applied to Cartesian and Non-Cartesian scans (2D, 3D, nD). In some examples, the position of each subset of data in k-space is distributed in k-space. For the vast majority of scans, this condition is already satisfied (e.g. for TSE with linear profile ordering) and/or can be satisfied with different profiles ordering strategies without loss of contrast/IQ.

Figure 10:
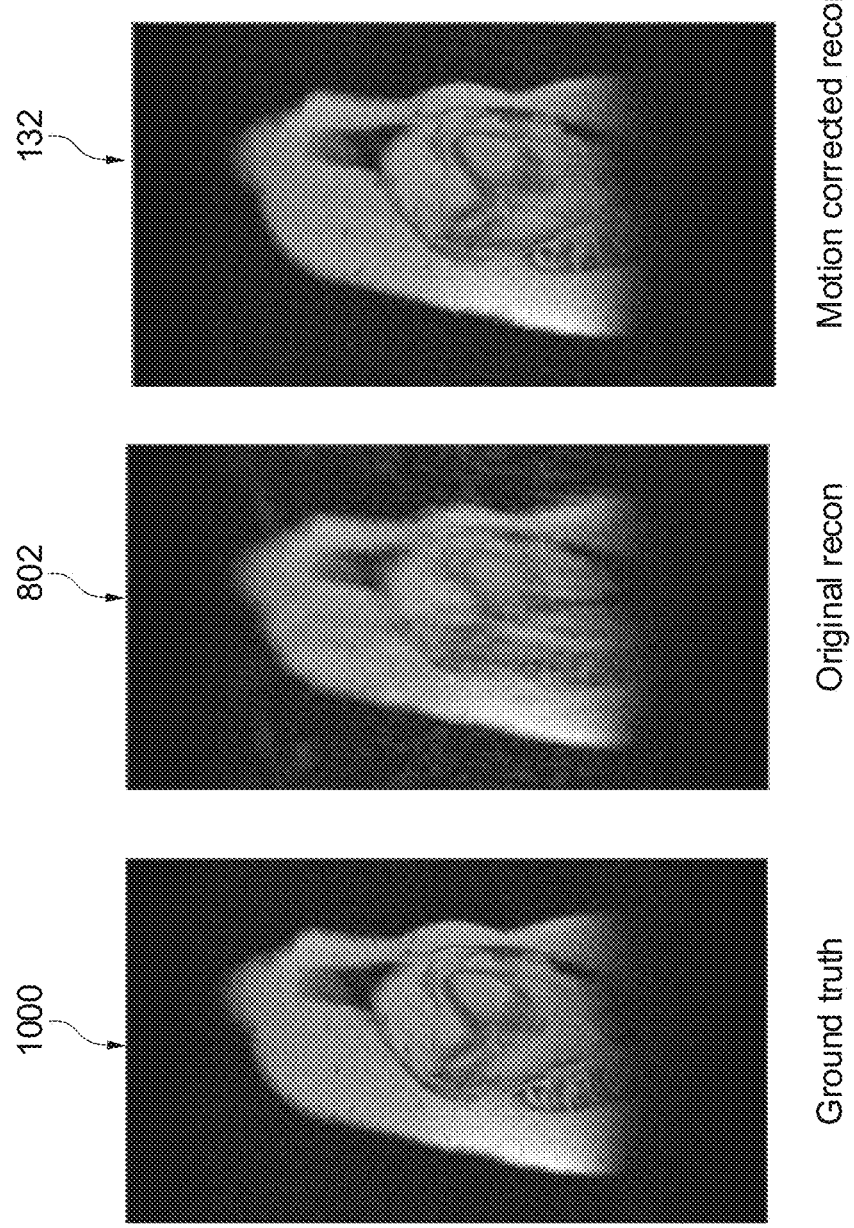
FIG. 10 shows a comparison of reconstructed magnetic resonance images to illustrate the benefit of the method of FIG. 8.
Figure 11:
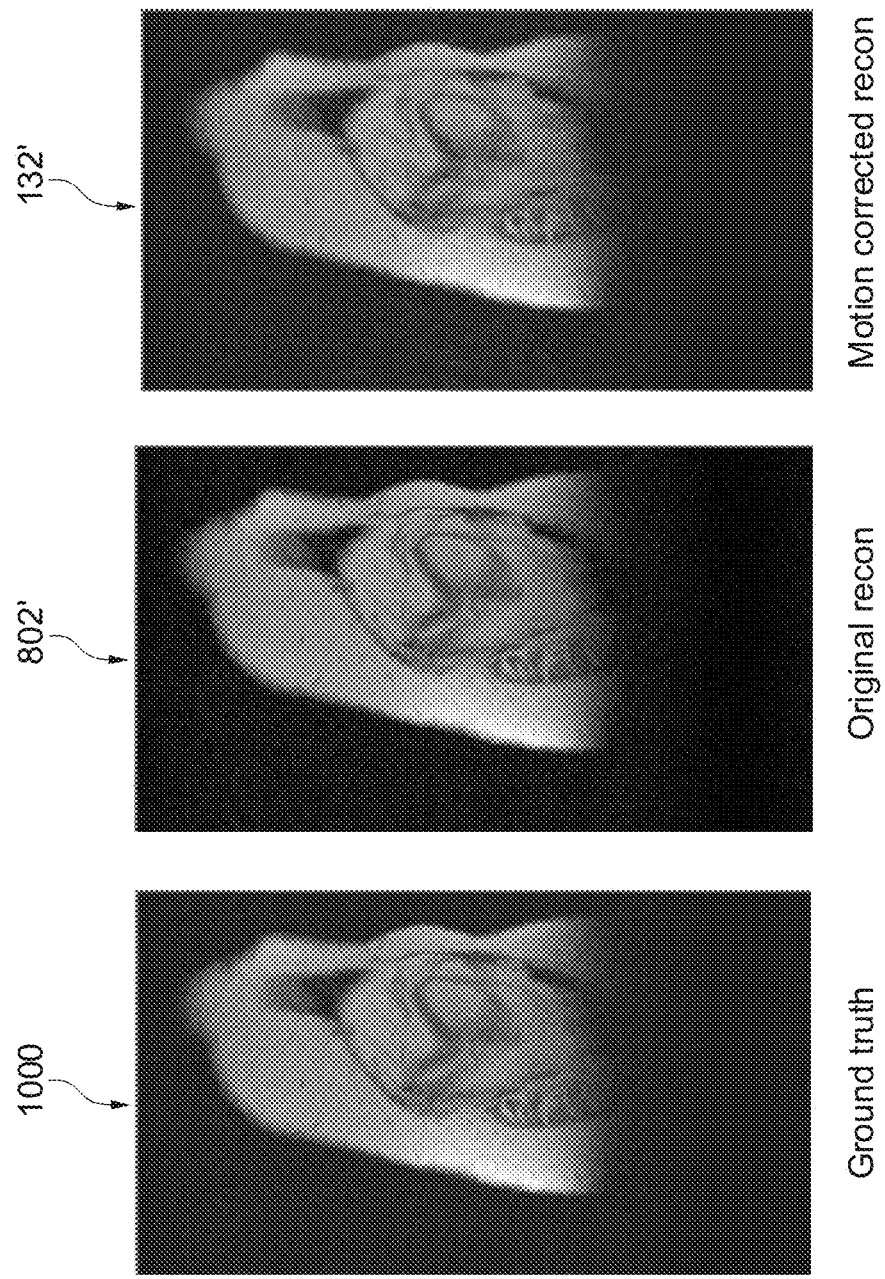
FIG. 11 shows a further comparison of reconstructed magnetic resonance images to illustrate the benefit of the method of FIG. 8.

Two examples of the performance are illustrated in FIGS. 10 and 11 below. Note that although this example is for single coil data, the same or even better performance is achieved for multi-coil data.

Some examples may use an AI based reconstructions on subsets of data from a scan resulting is a series of (non-diagnostic) images on the basis of which motion parameters are estimated for each subset of data. The estimated motion parameters (130 spatial transform data 130) are then used to correct the subsets of data (multiple groups of k-space data 126) after which the corrected data is used by a reconstruction using all data to produce the final (diagnostic) image(s) (the corrected magnetic resonance image 132, 132').

In one example, the estimated motion parameters and uncorrected subsets of data are used by a subsequent reconstruction to produce the final image(s). Here the motion parameters are used in the forward model.

Note that the final reconstruction can be any kind: a more 'classical' like C-SENSE or a 'newer' one based on Artificial Intelligence (e.g., RIM, DeepCascade, IstaNet, ADMM-Net, CycleGAN, Adaptive-CE-Net . . . ).

Examples may possibly include one or more of the following steps to reconstruct the corrected magnetic resonance image 132, 132' (see FIG. 8 below):
Acquire scan
Define multiple subsets of data (e.g. per shot or per time window)
Use Deep Learning) DL based reconstruction to generate image(s) for each subset of data
Use (standardly available) techniques/packages to estimate the motion parameters for each subset of data from the generated images. This can be rigid motion parameter of non-rigid motion parameters (e.g. deformation field). Examples include SIFT combined with RANSAC. Artificial intelligence motion based estimators such as DSAC may also be used.
Correct original subsets of data by using the estimated motion parameters
Use all corrected data in final reconstruction to produce final motion corrected image(s).

Figure 8:
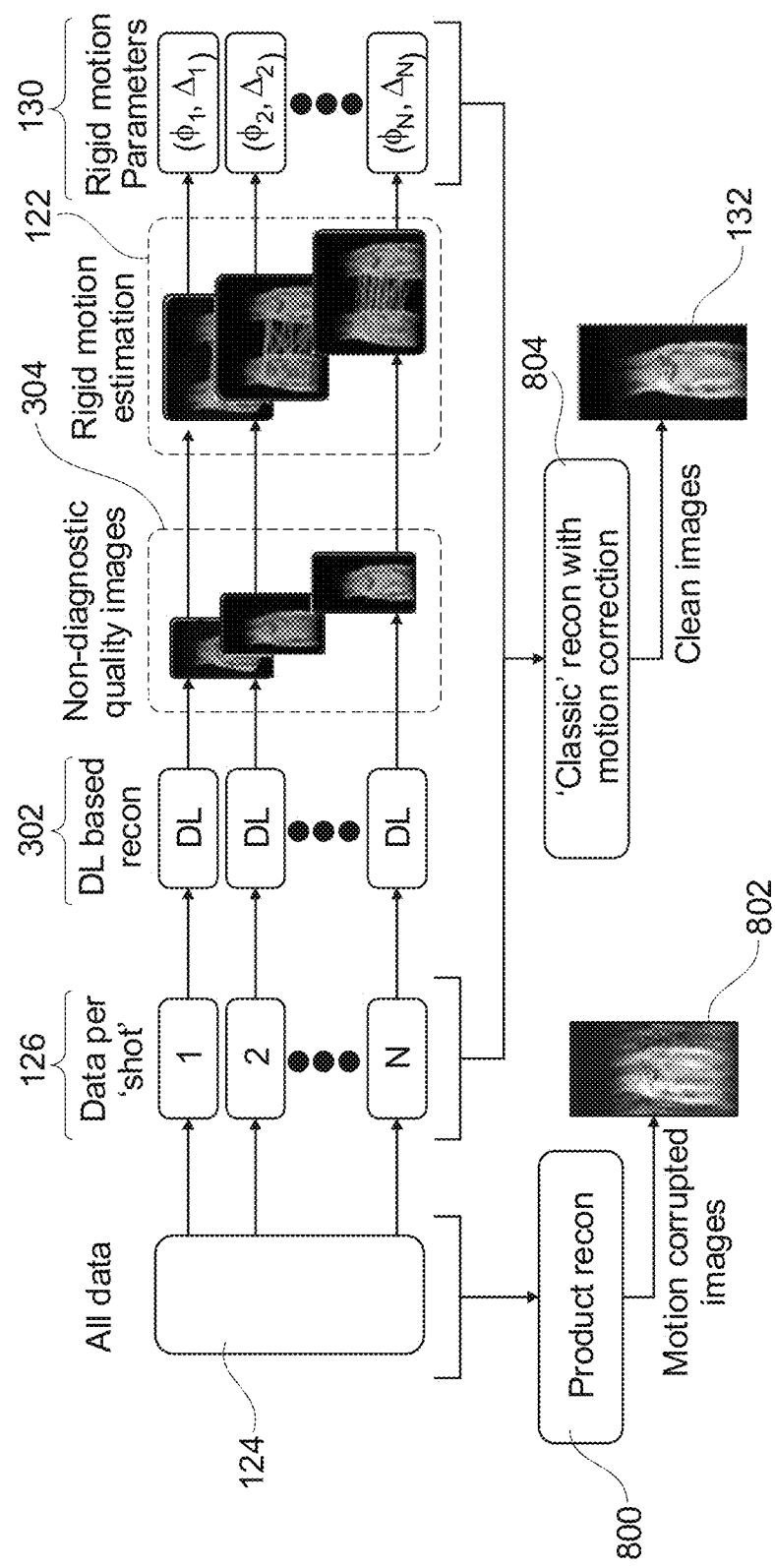
FIG. 8 shows a figure which graphically depicts a method of medical imaging.

FIG. 8 illustrates schematically a method of reconstructing the corrected magnetic resonance image 132. The k-space data 124 represents all data that was acquired during an acquisition. This data is divided into the multiple k-space data groups 126 which are labeled as data per shot or acquisition. Then the intermediate magnetic resonance imaging reconstruction neural network 302 is used. This is referred to as a DL or deep learning-based reconstruction. This results in the production of the intermediate magnetic resonance images 304 or the non-diagnostic quality images. Then in the next step, a straight spatial transformation estimation module 122 is used. In this example rigid motion estimation is used.

This is done by automatically identifying landmarks in two images that are compared and using this to generate the spatial transform data 130, which in this example are rigid motion parameters. The data per shot or the multiple k-space data groups 126 can be combined with the spatial transform data 130 or the rigid motion parameters and used in a classic or conventional reconstruction with motion correction 804. This then results in the production of the corrected magnetic resonance image 132. In contrast, the entire k-space data 124 can be reconstructed using a magnetic resonance imaging reconstruction without motion correction 800. This then results in a motion corrupted magnetic resonance image 802.

Instead of correcting the data prior to the final reconstruction, one can also incorporate the motion parameters in the forward model of the final reconstruction. The latter will be required when using non-rigid motion parameters (e.g. deformation field).

As was previously mentioned, two examples of the performance are given in FIG. 10 and FIG. 11 below. Note that although this example is for single coil data, the same or even better performance is achieved for multi-coil data.

Being able to deliver motion robust Cartesian scanning is of huge value because market adoption will be fast. Typically, the current motion robust products are non-Cartesian but these scans suffer from issues associated with non-Cartesian scanning, e.g. blurring and/or contrast issues.

As one example, the magnetic resonance imaging protocol can be: Motion robust Cartesian C-SENSE (or other parallel imaging technique with cartesian sampling of k-space) which will make a huge impact in the field.

Figure 9:
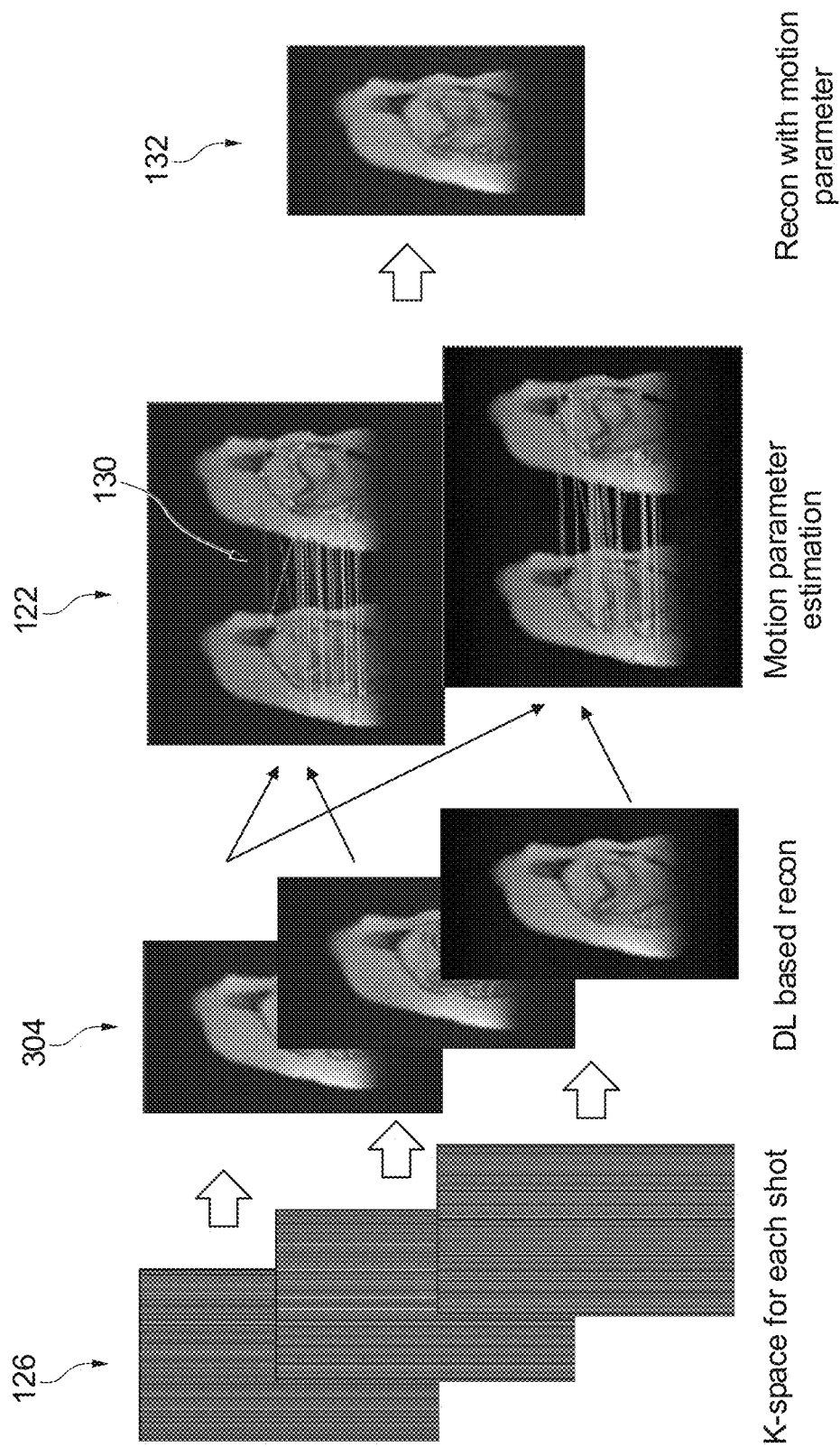
FIG. 9 further illustrates the method depicted in FIG. 8.

FIGS. 9 and 10 are used to illustrate the example of reconstructing the corrected magnetic resonance image 132 when there is more translational motion per shot. Images representing the multiple k-space data groups 126 are shown. These are then reconstructed using a deep learning-based method to construct the intermediate magnetic resonance images 304. In step 122 it can be seen how this is used to apply the spatial transformation estimation module 122 and what is illustrated exactly here is the rigid motion estimation. The combination of the multiple k-space data groups 126 and the spatial transform data 130 is used to reconstruct the corrected magnetic resonance image 132.

FIG. 10 compares three images, 1000, 802, and 132. The image 1000 represents a reconstruction using the k-space data 124 when there is no motion corruption. In step 802 groups of the k-space data have artificially had motion added to them. The reconstruction using this corrupted k-space data results in image 802 which is badly blurred. By applying a method as described herein the corrected magnetic resonance image 132 can be generated and it can be seen that most of the motion artefacts present in image 802 are now gone.

FIG. 11 shows a further example that is analogous to the example illustrated in FIGS. 9 and 10. Images 1000, 802', and 132' are compared. The same k-space data used in FIGS. 9 and 10 was used in FIG. 11 again. The image reconstructed using the uncorrupted k-space data is illustrated as image 1000 again. In this case large translational motion has been added per shot. When this corrupted k-space data is used to reconstruct an image it is badly blurred and the features are not recognizable. This motion corrupted image 802' is displayed next to image 1000. When the method, as described herein, is applied to the corrupted k-space data the corrected magnetic resonance image 132' is generated. It can be seen that the quality of the image 132' is almost the same as image 1000. FIGS. 9, 10, and 11 illustrate that the method is effective for both small motions and large translational motions.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS

100 medical system
102 computer
104 hardware interface
106 computational system
108 user interface
110 memory
120 machine executable instructions
122 spatial transformation estimation module
124 k-space data
126 multiple k-space data groups
128 reference k-space data group
130 spatial transform data
132 corrected magnetic resonance image
132' corrected magnetic resonance image
200 receive k-space data acquired according to a magnetic resonance imaging protocol
202 select one of the multiple k-space data groups as the reference k-space data group
204 calculate the spatial transform data for each of the multiple k-space data groups by inputting the multiple k-space data groups and the reference k-space data group into the spatial transformation estimation module
206 reconstruct the corrected magnetic resonance image according to the magnetic resonance imaging protocol using the multiple k-space data groups and the spatial transform data for each of the multiple k-space data groups
300 medical system
302 intermediate magnetic resonance imaging reconstruction neural network
304 intermediate magnetic resonance image
306 reference magnetic resonance image
400 receive the intermediate magnetic resonance image for each of the multiple k-space data groups by inputting each of the multiple k-space data groups into the intermediate magnetic resonance image reconstruction neural network
500 medical system
502 magnetic resonance imaging system
504 magnet
506 bore of magnet
508 imaging zone
509 region of interest
510 magnetic field gradient coils
512 magnetic field gradient coil power supply
514 radio-frequency coil
516 transceiver
518 subject
520 subject support
530 pulse sequence commands 600 acquire the k-space data by controlling the magnetic resonance imaging system with the pulse sequence commands
602 divide the k-space data into the multiple k-space data groups
700 medical system
702 subject motion monitor
730 subject motion data
800 magnetic resonance image reconstruction without motion correction
802 motion corrupted magnetic resonance image
804 magnetic resonance image reconstruction with motion correction
1000 motion free magnetic resonance image

The invention claimed is:

1. A medical system comprising:
a memory storing machine executable instructions, contains an intermediate magnetic resonance image reconstruction neural network and a spatial transformation estimation module, wherein the spatial transformation estimation module is configured for outputting spatial transform data descriptive of a spatial transform between a reference k-space data group and multiple k-space data groups in response to receiving the reference k-space data group and the multiple k-space data groups as input; wherein the intermediate magnetic resonance imaging reconstruction neural network is configured to output an intermediate magnetic resonance image in response to receiving a respective k-space data group; and
a computational system, wherein execution of the machine executable instructions causes the computational system to:
receive k-space data acquired according to a magnetic resonance imaging protocol by a Cartesian sampling pattern, wherein the k-space data is divided into the multiple k-space data groups that are disjoint in k-space;
select one of the multiple k-space data groups as the reference k-space data group;
reconstruct respective intermediate magnetic resonance images for the multiple k-space data groups and the reference k-space data group by inputting the multiple k-space data groups and the reference k-space data group into the intermediate magnetic resonance imaging reconstruction neural network;
calculate the spatial transform data for each of the multiple k-space data groups by inputting the respective intermediate magnetic resonance images for the multiple k-space data groups and the reference k-space data group into the spatial transformation estimation module for making a registration in image space between the respective intermediate magnetic resonance images for the multiple k-space data groups and the respective intermediate magnetic resonance image for the reference k-space data group; and
arrange to reconstruct a corrected magnetic resonance image according to the magnetic resonance imaging protocol using the multiple k-space data groups and the spatial transform data for each of the multiple k-space data groups.

2. The medical system of claim 1, wherein the reconstruction of the corrected magnetic resonance image is at least partially performed by calculating corrected multiple k-space data groups using the multiple k-space data groups and the spatial transform data for each of the multiple k-space data groups.

3. The medical system of claim 1, wherein the reconstruction of the corrected magnetic resonance image is performed as an optimization problem.

4. The medical system of claim 1, wherein the memory further contains a final magnetic resonance image reconstruction neural network configured to output a corrected magnetic resonance image in response to receiving multiple k-space data groups and the spatial transform data for each of the multiple k-space data groups, wherein the reconstruction of the corrected magnetic resonance image is performed by inputting the multiple k-space data groups and the spatial transform data for each of the multiple k-space data groups into the final magnetic resonance image reconstruction neural network.

5. The medical system of claim 1, wherein execution of the machine executable instructions further causes the computational system to divide the k-space data into the multiple k-space data groups according to any one of the following: by acquisition shots, by an acquisition time, by acquisition channel, a motion signal, and combinations thereof.

6. The medical system of claim 1, wherein the registration comprises a rigid body registration.

7. The medical system of claim 1, wherein the magnetic resonance imaging protocol is a parallel imaging magnetic resonance imaging protocol.

8. The medical system of claim 1, wherein the medical system further comprises a magnetic resonance imaging system, wherein the memory further contains pulse sequence commands configured for acquiring the k-space data according to the magnetic resonance imaging protocol, wherein execution of the machine executable instructions further causes the computational system to acquire the k-space data by controlling the magnetic resonance imaging system with the pulse sequence commands.

9. The medical system of claim 8, wherein the magnetic resonance imaging system comprises a radio frequency system with multiple receive channels, wherein the magnetic resonance imaging protocol is a parallel imaging magnetic resonance imaging protocol, wherein execution of the machine executable instructions further causes the computational system to divide the k-space data into the multiple k-space data groups at least partially according to the receive channels.

10. The medical system of claim 8, wherein the machine executable instructions further causes the computational system to divide the k-space data into the multiple k-space data groups at least partially according to any one of the following:
by acquisition shots;
by an acquisition time or acquisition interval; and
combinations thereof.

11. The medical system of claim 8, wherein the medical system further comprises a subject motion monitor configured for generating subject motion data descriptive of a motion or position of the subject, wherein execution of the machine executable instructions further causes the computational system to:
control the subject motion monitor to acquire the subject motion data during acquisition of the k-space data; and
divide the k-space data into the multiple k-space data groups at least partially according to the subject motion data.

12. The medical system of claim 1, wherein the spatial transformation estimation module comprises a spatial transformation estimating neural network.

13. A method of medical imaging, wherein the method comprises:
receiving k-space data acquired by a Cartesian sampling pattern according to a magnetic resonance imaging protocol, wherein the k-space data is divided into multiple k-space data groups that are disjoint in k-space;
selecting one of the multiple k-space data groups as a reference k-space data group;
reconstructing respective intermediate magnetic resonance images for the multiple k-space data groups and the reference k-space data group by inputting the multiple k-space data groups and the reference k-space data group into an intermediate magnetic resonance imaging reconstruction neural network;
calculating spatial transform data for each of the multiple k-space data groups using the respective intermediate magnetic resonance images by making a registration in image space between the respective intermediate magnetic resonance images for the multiple k-space data groups and the respective intermediate magnetic resonance image for the reference k-space data group; and
reconstructing a corrected magnetic resonance image according to the magnetic resonance imaging protocol using the multiple k-space data groups and the spatial transform data for each of the multiple k-space data groups.

14. The method of claim 13, wherein reconstructing the corrected magnetic resonance image comprises calculating corrected multiple k-space data groups using the multiple k-space data groups and the spatial transform data for each of the multiple k-space data groups.

15. The method of claim 13, wherein reconstructing the corrected magnetic resonance image comprises performing an optimization problem.

16. The method of claim 13, further comprising dividing the k-space data into the multiple k-space data groups according to at least one of acquisition shots, an acquisition time, acquisition channel, or a motion signal.

17. The method of claim 13, wherein the registration comprises rigid body registration.

18. The method of claim 13, wherein the magnetic resonance imaging protocol is a parallel imaging magnetic resonance imaging protocol.

19. A non-transitory computer readable medium storing machine executable instructions for execution by a computational system, wherein execution of the machine executable instructions causes the computational system to:
receive k-space data acquired by a Cartesian sampling pattern according to a magnetic resonance imaging protocol, wherein the k-space data is divided into multiple k-space data groups that are disjoint in k-space;
select one of the multiple k-space data groups as a reference k-space data group;
reconstruct respective intermediate magnetic resonance images for the multiple k-space data groups and the reference k-space data group by inputting the multiple k-space data groups and the reference k-space data group into an intermediate magnetic resonance imaging reconstruction neural network;
calculate spatial transform data for each of the multiple k-space data groups using the respective intermediate magnetic resonance images by making a registration in image space between the respective intermediate magnetic resonance images for the multiple k-space data groups and the respective intermediate magnetic resonance image for the reference k-space data group; and
arrange to reconstruct a corrected magnetic resonance image according to the magnetic resonance imaging protocol using the multiple k-space data groups and the spatial transform data for each of the multiple k-space data groups.

20. The non-transitory computer readable medium of claim 19, wherein execution of the machine executable instructions further causes the computational system to divide the k-space data into the multiple k-space data groups according to at least one of acquisition shots, an acquisition time, acquisition channel, or a motion signal.

* * * * *